US009622877B2

(12) United States Patent
Erbulut et al.

(10) Patent No.: US 9,622,877 B2
(45) Date of Patent: Apr. 18, 2017

(54) DISC PROSTHESIS

(71) Applicant: Koc Universitesi, Sariyer, Istanbul (TR)

(72) Inventors: Deniz Ufuk Erbulut, Istanbul (TR); Ali Fahir Ozer, Istanbul (TR); Ismail Lazoglu, Istanbul (TR)

(73) Assignee: Koc Universitesi, Istanbul (TR)

(*) Notice: Subject to any disclaimer, the term of this patent is extended or adjusted under 35 U.S.C. 154(b) by 238 days.

(21) Appl. No.: 14/773,714

(22) PCT Filed: Mar. 7, 2013

(86) PCT No.: PCT/EP2013/054656
§ 371 (c)(1),
(2) Date: Sep. 8, 2015

(87) PCT Pub. No.: WO2013/132028
PCT Pub. Date: Sep. 12, 2013

(65) Prior Publication Data
US 2016/0166400 A1 Jun. 16, 2016

(30) Foreign Application Priority Data
Mar. 9, 2012 (TR) .................. 2012 02712

(51) Int. Cl.
A61F 2/44 (2006.01)
A61F 2/30 (2006.01)

(52) U.S. Cl.
CPC .. A61F 2/4425 (2013.01); A61F 2002/30247 (2013.01); A61F 2002/30299 (2013.01);
(Continued)

(58) Field of Classification Search
CPC .................................................... A61F 2/4425
See application file for complete search history.

(56) References Cited

U.S. PATENT DOCUMENTS 5,895,428 A 4/1999 Berry
2005/0187632 A1 8/2005 Zubok et al.
(Continued)

FOREIGN PATENT DOCUMENTS

WO WO 2006/004848 A1 1/2006

OTHER PUBLICATIONS

International Preliminary Report on Patentability, dated Jul. 2, 2014, pp. 1-5, issued in International Application No. PCT/EP2013/054656, European Patent Office, Berlin, Germany.
(Continued)

Primary Examiner — Andrew Yang
(74) Attorney, Agent, or Firm — Brinks Gilson & Lione

(57) ABSTRACT

A disc prosthesis comprising an upper cover provided with a cavity and a curved surface; a bearing member comprising an outer surface, on which the upper cover can rotate and received by the cavity, and at least one mount; a movement member which is provided with an outer surface compatible with an inner surface of the mount, and which is received by the mount so as to move concurrently with the upper cover; a lower cover provided with a cavity to receive said mount and a curved surface; and a connection member extending from the cavity towards the lower cover and being mounted to the movement member by being passed through a channel which extends along the bearing member and is in connection with said mount so as to connect the bearing member to the upper cover.

11 Claims, 3 Drawing Sheets

(52) U.S. Cl.
CPC .............. *A61F 2002/30331* (2013.01); *A61F 2002/30362* (2013.01); *A61F 2002/30662* (2013.01); *A61F 2002/443* (2013.01); *A61F 2230/0071* (2013.01); *A61F 2310/00023* (2013.01)

(56) References Cited

U.S. PATENT DOCUMENTS

2006/0229725 A1  10/2006  Lechmann et al.
2008/0221689 A1   9/2008  Chaput et al.

OTHER PUBLICATIONS

International Search Report and Written Opinion of the International Searching Authority, dated Aug. 8, 2013, pp. 1-10, issued in International Application No. PCT/EP2013/054656, European Patent Office, Berlin, Germany.
Written Opinion of the International Preliminary Examining Authority (PCT Rule 66); dated Mar. 17, 2014, pp. 1-7, issued in International Application No. PCT/EP2013/054656, European Patent Office, Berlin, Germany.

DISC PROSTHESIS

BACKGROUND

The present disclosure relates to a disc prosthesis for use in the treatment of spinal disorders (particularly in the cervical region thereof).

The spine is made up of a series of connected bones called as the vertebra and assumes the main functions of carrying the body weight, constituting the body, etc. The vertebrae are connected by a disc and two small joints which are called as the facet joints. These disc and facet joints in the spine allow for movements, for bending, and particularly for turning the neck and the back. The disc is made up of strong connective tissues connecting one vertebra to the next and acts as a cushion or shock absorber between the vertebrae. The structure of the spine is preserved because the movement is restricted to those vertebrae which are proximate to each other due to the shape and the condition of the articular surfaces and the strong braking effects in the vertebrae, because the movements of the spine are spread over many joints, and because the movement between neighbouring vertebrae is low. Having said that, the spine is capable of making movements in many various directions as a result of the concurrent movements occurring in many vertebrae.

Due to aging and negative conditions (e.g. accidents, incorrect body movements), degenerative disorders are seen in the discs, which separate the vertebrae from each other and affect connecting flexible and fibrous tissues. In a disease called as the hernia, for instance, the fibrous tissue ring covering the flexible center of the disk weakens so that the disc center protrudes and exerts pressure to the spine or to the regions where the nerve roots protrudes from between the vertebrae. The regions of the spine at which this is most frequently encountered are the lower part of the waist (i.e. the lumbar region) and the cervical region. Disc prostheses, which are capable of preventing or mitigating the pressure exerted by the discs to the spine and to the nerves, can be used in the treatment of these degenerative diseases.

BRIEF DESCRIPTION

A disc prosthesis developed for use in the treatment of spinal disorders comprises at least one upper cover provided with at least one upper cavity and at least one curved surface contacting the vertebrae; at least one bearing member comprising at least one bearing outer surface on which the upper cover can make a rotational movement and which is structurally compatible with the upper cavity on the upper cover so as to be received by said upper cavity, and at least one mount extending in the form of a keel or projection; at least one movement member, which is provided with at least one movement member outer surface which is compatible with the inner surface of the mount of the bearing member, and which is received by this mount such that the movement member can move together with the upper cover; at least one lower cover provided with at least one lower cavity which is compatible to receive said mount and at least one outward curved surface on the side thereof making contact with the vertebrae; and at least one connection member extending in the form of a keel from the upper cavity on the upper cover towards the lower cover and being mounted to said movement member by being passed through at least one channel which extends along the bearing member and is in connection with said mount so as to connect the bearing member to the upper cover such that the upper cover can be moved on the bearing member.

The disc prosthesis may move in harmony with the movement of the spine without restricting normal body movements. Additionally, mistakes which may arise from surgical intervention may be minimized by virtue of the fact that the disc prosthesis according to the present invention may be applied to the spine in a monolithic form.

An aspect of an embodiment is to develop a disc prosthesis which may be used in the treatment of spinal disorders.

Another aspect of an embodiment is to develop a disc prosthesis which may be used in the treatment of disorders which occur particularly in the cervical region of the spine.

Another aspect of an embodiment is to develop a disc prosthesis which has a long use-life.

Another aspect of an embodiment is to develop a disc prosthesis which can move in harmony with normal body movements without imposing any restrictions thereon.

Another aspect of an embodiment is to develop a disc prosthesis which can be easily placed between the vertebrae.

Another aspect of an embodiment is to develop a disc prosthesis by which a uniform load distribution is provided over the vertebrae by virtue of the multidirectional movement capability of the disc prosthesis.

Another aspect of an embodiment is to develop a disc prosthesis by which any injury of the contacting vertebrae is prevented.

BRIEF DESCRIPTION OF THE DRAWINGS

Illustrative embodiments of the disc prosthesis are shown in the accompanying figures briefly described hereunder.

The parts in said figures are individually referenced as following.

| | |
|---|---|
| Disc prosthesis | (P) |
| Upper cover | (K1) |
| Lower cover | (K2) |
| Curved surface | (C) |
| Bearing member | (1) |
| Mount | (1a) |
| Inner surface | (1b) |
| Bearing outer surface | (1c) |
| Channel | (1e) |
| Orifice | (2a) |
| Movement member outer surface | (2b) |
| Keel | (3, 4) |
| Movement member | (2) |
| Connection member | (5) |
| Upper Cavity | (6) |
| Lower Cavity | (6a) |

DETAILED DESCRIPTION

Disc prostheses used in the treatment of spinal disorders may decrease the life quality of the patients carrying such prostheses when the prostheses become worn out or cannot comply with the normal body movements in time. Additionally, such disc prostheses may cause the respective operator to loose time since they are placed with difficulty in between the vertebrae during surgery. Accordingly, a disc prosthesis may be desirable which can comply with normal body movements, can easily be placed to the spine, and has a long use-life.

Figure 1:
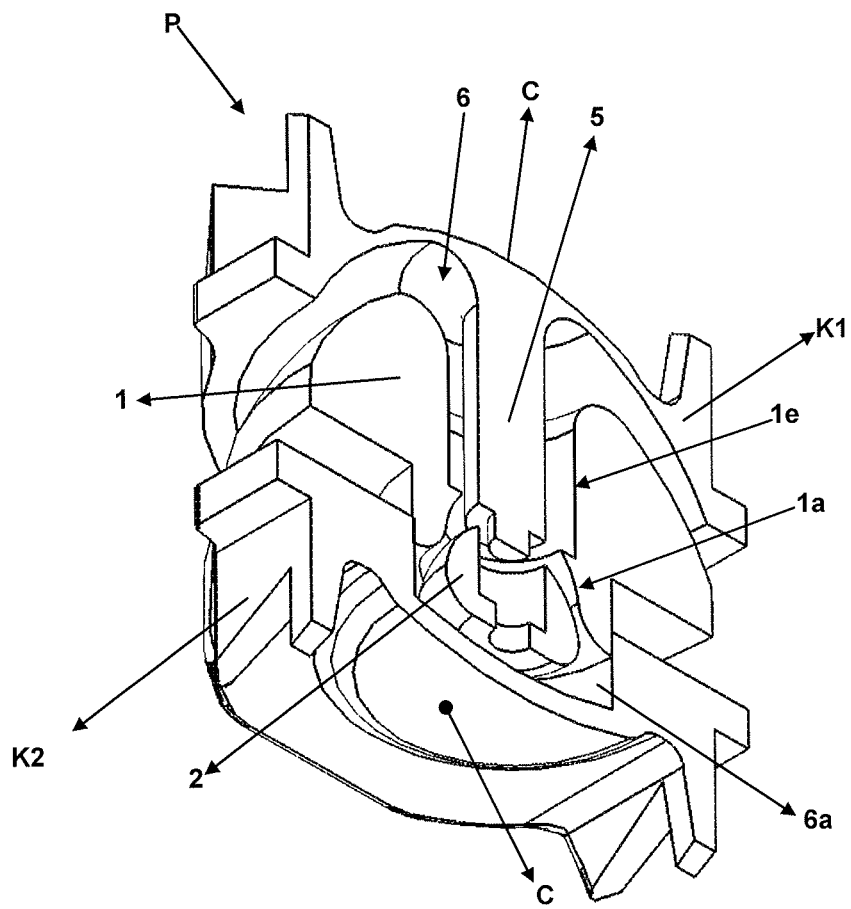
FIG. 1 is a perspective bottom view of semi-exploded section of a disc prosthesis.
Figure 2:
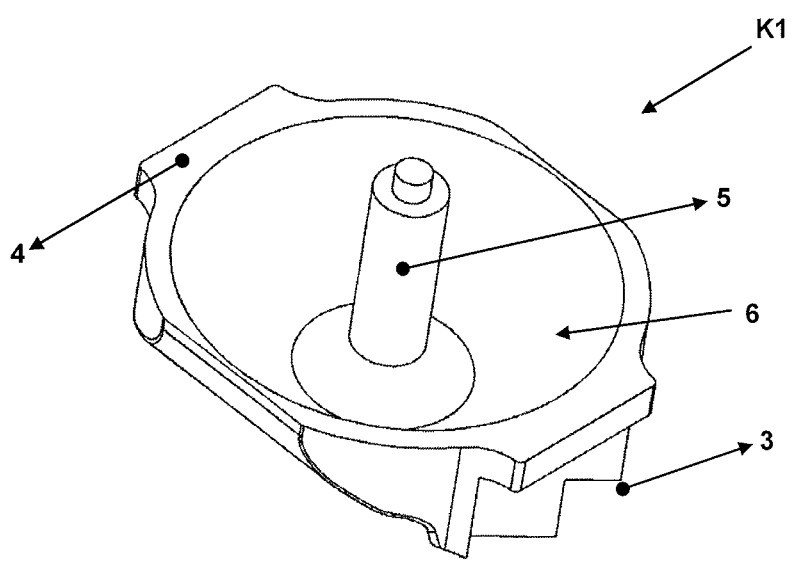
FIG. 2 is a view of an upper cover comprised by the disc prosthesis.
Figure 3:
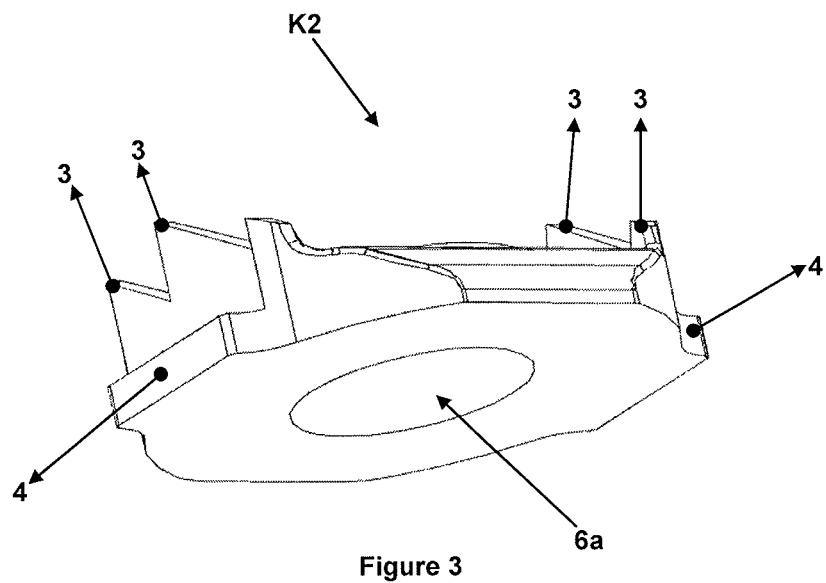
FIG. 3 is a perspective bottom view of a lower cover comprised by the disc prosthesis.
Figure 4:
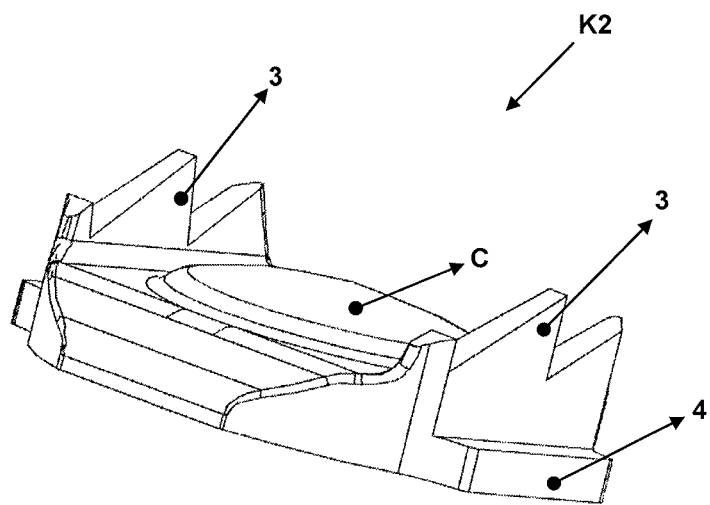
FIG. 4 is a perspective top view of the lower cover.
Figure 5:
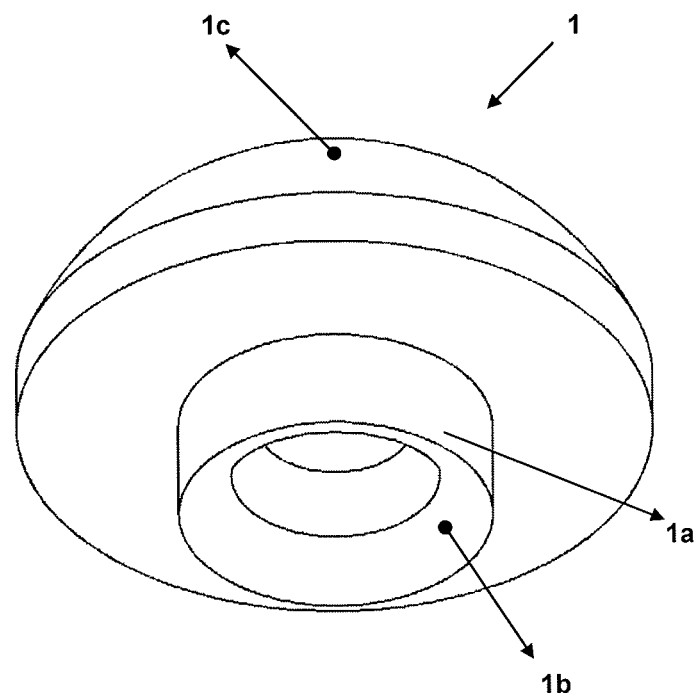
FIG. 5 is a perspective bottom view of a bearing member comprised by the disc prosthesis.
Figure 6:
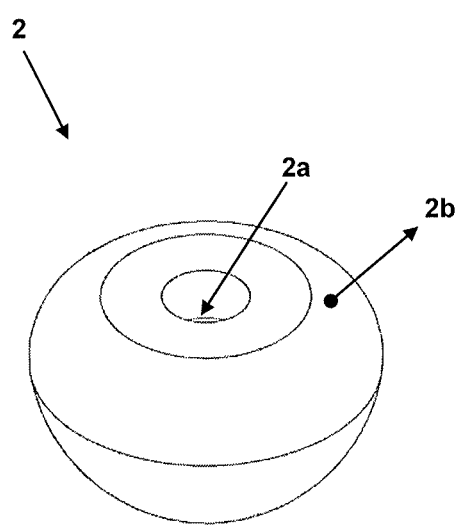
FIG. 6 is a top view of a movement member comprised by the disc prosthesis.

The disc prosthesis (P), shown in a perspective, semi-exploded view from bottom is given in FIG. 1 comprises at least one upper cover (K1) (for a detailed view thereof see FIG. 2) provided with at least one upper cavity (6) having preferably a semi-spherical form and with at least one curved surface (C) contacting the vertebrae; at least one bearing member (1) (for a detailed view thereof see FIG. 5) comprising at least one bearing outer surface (1c), on which the upper cover (K1) can make a rotational movement and which has a structure compatible with and received by the upper cavity (6) on the upper cover (K1), and at least one mount (1a) extending in the form of a keel or projection and having preferably a sloped inner surface (1b); at least one movement member (2) (for a detailed view thereof see FIG. 6), which is provided with at least one movement member outer surface (2b) which is compatible with the inner surface (1b) of the mount (1a) provided in the bearing member (1), and which is received by this mount (1a) so as to move concurrently with the upper cover (K1); at least one lower cover (K2) provided with at least one lower cavity (6a) which is compatible to receive said mount (1a) and at least one outward curved surface (C) on the side thereof making contact with the vertebrae; and at least one connection member (5) extending in the form of a keel from the upper cavity (6) on the upper cover (K1) towards the lower cover (K2) and being mounted to said movement member (2) (preferably by being received by at least one orifice (2a) provided in the movement member (2)) by being passed through at least one channel (1e) which extends along the bearing member (1) and is in connection with said mount (1a) so as to connect the bearing member (1) to the upper cover (K1) such that the upper cover (K1) can be moved on the bearing member (1). Said connection member (5) may either have a monolithic structure with the upper cover (K1), or may be an external part connecting the bearing member (1) to the upper cover (K1).

In the disc prosthesis developed for spinal disorders (preferably for those which occur at the cervical region thereof), the bearing member (1) has a fixed position between the upper cover (K1) and the movement member (2) and is in surface contact with the upper cover (K1) and the movement member (2). In addition, the upper cover (K1) can rotate on the bearing member (1) and the movement member (2) can move in the mount (1a) disposed in the bearing member (1) since the movement member (2) is in contact with the inner surface (1b) of this mount (1a). Thus the movement member (2) can move synchronously with the upper cover (K1) and allow both for the rotational movement (axial rotation) of the spine and for the horizontal and vertical movements (extension/flexion and lateral movements) thereof. It is thus possible to develop disc prosthesis (P) which can move in compliance with the movements of the spine without restricting the normal body movements. Additionally, an incorrect placement of the disc prosthesis (P) to the spine can be avoided by virtue of the fact that the disc prosthesis (P) according to the present invention can be placed to the spine in a monolithic form. Furthermore, the disengagement of the upper cover (K1) and the bearing member (1) is prevented during the movement of the spine by virtue of the connection member (5) and the movement member (2) comprised by the disc prosthesis (P), and the engagement between the upper cover (K1), the bearing member (1), the movement member (2), and the lower cover (K2) is safely ensured when the bearing member (1) is placed into the lower cavity (6a) disposed in the lower cover (K2).

In a preferred embodiment of the present invention, at least one keel (3) enabling to retain the disc prosthesis (P) vertically with respect to the spine is provided on the upper cover (K1) and/or lower cover (K2), as representatively illustrated in FIGS. 1-4. By virtue of this keel (3), the disc prosthesis (P) can be retained on the vertebrae in a firm manner and the dislocation thereof is prevented when the spine is moving.

In another preferred embodiment of the present invention, the disc prosthesis (P) comprises at least one other keel (4), which is disposed on the upper cover (K1) and/or lower cover (K2) and by which the disc prosthesis (P) contacts the lateral sides of the vertebrae. By virtue of said keel (4), the disc prosthesis (P) can be retained on the vertebrae in a safer manner and the dislocation of the disc prosthesis (P) from the site of placement is prevented when the spine is moving. Additionally, by virtue of this keel (4), the load exerted by the spine to the site where the disc prosthesis (P) is located (the vertebrae) is distributed uniformly over the vertebrae so that the latter is prevented against injuries.

In an alternative embodiment of the present invention, the bearing member (1) comprises preferably a polyethylene (e.g. an ultrahigh molecular weight polyethylene (UHMWPE)) material, whereas the movement member (2) and the covers (K1, K2) comprise preferably a titanium alloy (e.g. titanium 6-aluminum 4-vanadium (Ti6Al4V)) material. Thus, the abrasion which may arise from the friction between the movement member (2) and the bearing member (1) can be minimized during the movement of the disc prosthesis (P).

In another preferred embodiment of the present invention, the movement member (2) is disposed in the lower cavity (6a) of the lower cover (K2) in a suspending manner without making contact with the lower cover (K2). Thus, the restriction of the movement of the movement member (2) can be prevented. Additionally, by virtue of a tight fit of the mount (1a) in the form of a protrusion disposed in the bearing member (1) to the lower cavity (6a) provided in the lower cover (K2), the disengagement of the components (K1, K2, 1, 2) making up the disc prosthesis (P) can be prevented.

A disc prosthesis (P) may be developed with the present disclosure, which can move in compliance with the movements of the spine without restricting the normal body movements. Additionally, the disc prosthesis (P) developed according to the present disclosure does not injure the vertebrae during the movement of the spine, and mistakes which may arise from a surgical intervention can be minimized with the disc prosthesis (P) being placed to the spine in a monolithic form.

The invention claimed is:

1. A disc prosthesis for use in the treatment of spinal disorders, comprising
   at least one upper cover provided with at least one upper cavity and at least one upper curved surface configured to contact a vertebrae;
   at least one bearing member comprising at least one bearing outer surface, on which the upper cover can make a rotational motion and which is structurally compatible with and receivable by the upper cavity on the upper cover, and at least one mount extending in the form of a projection and having an inner surface with a partial spherical shape;

at least one movement member, which is provided with at least one movement member outer surface which is in contact and compatible with said inner surface of the mount provided in the bearing member, and which is received by this mount so as to allow rotational, horizontal, and vertical movements with respect to bearing member and synchronous movement with the upper cover;

at least one lower cover provided with at least one lower cavity which is compatible to receive said mount, wherein said mount is fixed to the lower cavity disposed in the lower cover by means of a friction fit, and at least one lower outward curved surface on the side thereof is configured to contact the vertebrae;

at least one connection member extending from the upper cavity on the upper cover towards the lower cover and being mounted to said movement member by being passed through at least one channel which extends along the bearing member and is in connection with said mount so as to connect the bearing member to the upper cover such that the upper cover can be moved on the bearing member and so as to prevent disengagement of the upper cover and the bearing member.

2. The disc prosthesis according to claim 1, wherein said upper cavity has a semi-spherical form.

3. The disc prosthesis according to claim 1, wherein said connection member is monolithic with the upper cover.

4. The disc prosthesis according to claim 1, further comprising at least one first keel disposed on at least one of the upper cover and the lower cover for retaining the disc prosthesis vertically with respect to the spine.

5. The disc prosthesis according to claim 4, further comprising at least one second keel, which is disposed on the at least one of the upper cover and the lower cover and by which the disc prosthesis is configured to contact the vertebrae by the lateral sides of the first keel and a second keel.

6. The disc prosthesis according to claim 1, characterized in that the bearing member comprises a polyethylene material.

7. The disc prosthesis according to claim 6, wherein the polyethylene material is ultra high molecular weight polyethylene.

8. The disc prosthesis according to claim 1, wherein the movement member, the upper cover and the lower cover comprise a titanium alloy material.

9. The disc prosthesis according to claim 8, wherein said titanium alloy material is titanium 6-aluminum 4-vanadium.

10. The disc prosthesis according to claim 1, further comprising at least one orifice disposed in the movement member to connect said connection member to the movement member.

11. The disc prosthesis according to claim 1, wherein the movement member is disposed in the lower cavity of the lower cover in a suspending manner without making contact with the lower cover.

\* \* \* \* \*